(12) United States Patent
Tucker et al.

(10) Patent No.: US 9,649,349 B1
(45) Date of Patent: May 16, 2017

(54) SYSTEM AND METHOD FOR PRODUCING A TERPENE-ENHANCED CANNIBINOID CONCENTRATE

(71) Applicants: Gary Tucker, Hayfork, CA (US); William Lee Fulton, Oregon City, OR (US)

(72) Inventors: Gary Tucker, Hayfork, CA (US); William Lee Fulton, Oregon City, OR (US)

(73) Assignee: METAMORPHIC ALCHEMY & DISTILLATIONS, INC., Hayfork, CA (US)

( * ) Notice: Subject to any disclaimer, the term of this patent is extended or adjusted under 35 U.S.C. 154(b) by 0 days.

(21) Appl. No.: 15/410,289

(22) Filed: Jan. 19, 2017

(51) Int. Cl.
| | |
|---|---|
| *A01N 65/00* | (2009.01) |
| *A61K 36/185* | (2006.01) |
| *A61K 31/352* | (2006.01) |
| *A61K 31/05* | (2006.01) |
| *B01D 11/02* | (2006.01) |
| *B01D 3/12* | (2006.01) |
| *B01D 37/00* | (2006.01) |
| *B01D 3/42* | (2006.01) |

(52) U.S. Cl.
CPC ............ *A61K 36/185* (2013.01); *A61K 31/05* (2013.01); *A61K 31/352* (2013.01); *B01D 3/12* (2013.01); *B01D 3/42* (2013.01); *B01D 11/0203* (2013.01); *B01D 11/0288* (2013.01); *B01D 37/00* (2013.01); *A61K 2236/15* (2013.01); *A61K 2236/37* (2013.01); *A61K 2236/51* (2013.01); *A61K 2236/55* (2013.01)

(58) Field of Classification Search
CPC ....................................................... A61K 36/00
USPC ........................................................... 424/725
See application file for complete search history.

(56) References Cited

FOREIGN PATENT DOCUMENTS

CA            2911168      *   5/2015

* cited by examiner

*Primary Examiner* — Michael Meller
(74) *Attorney, Agent, or Firm* — Arc IP Law, PC; Joseph J. Mayo

(57) ABSTRACT

A system and method of producing a blended extract of cannabinoids and terpenes, which extracts terpenes using supercritical CO2, and extracts a cannabinoid concentrate from the residual material using a cold ethanol flush followed by distillation; the CO2-extracted terpenes are then added back to the cannabinoid concentrate in a final blending step. Blending terpenes at the end of extraction may enhance the flavor and effectiveness of the cannabinoid concentrate. By separately extracting terpenes and cannabinoids, optimal processes and parameters may be used for each step. Blending may combine terpenes and cannabinoids in any desired ratio; for example, a terpene-to-cannabinoid ratio of approximately 1:10 may be used. The ethanol used in the cold ethanol extraction of cannabinoids may be recovered and reused for subsequent batches. Cannabinoid concentrates may be redistilled multiple times to enhance their concentration, followed by terpene blending.

16 Claims, 9 Drawing Sheets

SYSTEM AND METHOD FOR PRODUCING A TERPENE-ENHANCED CANNIBINOID CONCENTRATE

BACKGROUND OF THE INVENTION

Field of the Invention

One or more embodiments of the invention are related to the field of extraction of substances from plant material. More particularly, but not by way of limitation, one or more embodiments of the invention enable a system and method for producing a terpene-enhanced cannabinoid concentrate from *cannabis* plant material.

Description of the Related Art

Several methods for extracting cannabinoids from *cannabis* plant material are known in the art. A limitation of many of these methods is that the terpenes in the *cannabis* plant are often lost or greatly reduced in the final extracted product. While cannabinoids provide a major element of the medicinal or psychoactive effect of *cannabis*, the many terpenes in the *cannabis* plant also contribute significantly to the plant's properties.

*Cannabis* processors have explored techniques to simultaneously extract cannabinoids and preserve terpenes, with limited success. Processes and parameters that are optimal for cannabinoid extraction may be ineffective for terpene extraction, and vice-versa. Moreover, tuning the ratio of terpenes to cannabinoids is difficult or impossible when attempting to extract both simultaneously. A potential solution to these difficulties, which is not known in the art, is to combine separate procedures for terpene extraction and *cannabis* extraction, and to blend the outputs of these procedures into a final product. This approach allows optimal processes and parameters to be used for each step, and it provides maximum flexibility for the composition of the final blend. There are no known methods that use such an approach to generate a terpene-enhanced cannabinoid concentrate. In addition, the only method known in the art for terpene extraction is steam distillation, which extracts a limited profile of terpenes because it is water based. There is a need for combining a more effective terpene extraction process with a blending process that combines terpenes and cannabinoids.

For at least the limitations described above there is a need for a system and method for producing a terpene-enhanced cannabinoid concentrate.

BRIEF SUMMARY OF THE INVENTION

One or more embodiments described in the specification are related to a system and method for producing a terpene-enhanced cannabinoid concentrate. Embodiments of the invention combine an extraction process for terpene oil and an extraction process for cannabinoids, to yield a blend with combined benefits of terpenes and cannabinoids.

One or more embodiments of the invention may produce a terpene-enhanced cannabinoid concentrate using the following steps: *Cannabis* plant material is ground, then exposed to a carbon dioxide solvent, for example using a supercritical CO2 fluid. The CO2 extracts terpene oil and terpene hydrosols from the *cannabis*. The residual plant material (after CO2 extraction) is then washed with cold ethanol, and the resulting ethanol oil solution is separated into ethanol (which may be recycled) and *cannabis* oil. The *cannabis* oil is then distilled to obtain cannabinoid distillates. These cannabinoid distillates are blended with the terpene oil from CO2 extraction, yielding a terpene-enhanced cannabinoid concentrate. Terpenes may for example add flavor to the cannabinoid concentrate or enhance the effects of the concentrate.

Cannabinoid distillates may include any or all of Tetrahydrocannabinolic Acid (THCa), Tetrahydrocannabinol (THC), Tetrahydrocannabivarin (THCV), Cannabidolic Acid (CBDa), Cannabidiol (CBD), Cannabichromene (CBC), Cannabigerol (CBG), and Cannabinol (CBN). In one or more embodiments, the concentration of cannabinoids in the cannabinoid distillates may be 80% or higher. The cannabinoid distillates may be optionally redistilled (multiple times if desired) to increase the cannabinoid concentration.

Terpenes extracted in the terpene oil and terpene hydrosols may include any or all of alpha-Bisabolol, Camphene, 3-Carene, beta-Caryophyllene, Citronellol, Cymene, Eucalyptol, Famesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene.

Terpene oil and cannabinoid concentrate may be combined in any ratio. In one or more embodiments, the ratio by volume of terpene oil to cannabinoid concentrate may be in the range of 1:25 to 1:5. In one or more embodiments the ration may be in the range of 1:12 to 1:8. As an illustration, one or more embodiments may generate a blend with a terpene-to-cannabinoid concentrate ratio of approximately 1:10.

Illustrative parameters used for CO2 extraction of terpene oil and terpene hydrosol in one or more embodiments may include for example: CO2 pressure in the range of 1000 psi to 1300 psi, forming a supercritical fluid; temperature between 80 F and 100 F; and elapsed time of exposing the *cannabis* plant material to the supercritical CO2 in the range of 15 minutes to 6 hours. After CO2 extraction and removal of CO2 (for example by reducing pressure to allow the CO2 to evaporate), the terpene oil and terpene hydrosol may be filtered at a temperature between −80 F and 40 F, using a filter with pore size greater than 0.25 micron.

Illustrative parameters used for cold ethanol extraction and ethanol recovery in one or more embodiments may include for example: flushing of residual plant material with cold ethanol at a temperature of 30 F or below; and distilling the ethanol oil solution at a temperature between 120 F and 165 F under a vacuum between 10 inches Hg and 25 inches Hg. Recovered ethanol may be optionally reused for subsequent washing of a second batch of material.

Distilling of *cannabis* oil into cannabinoid distillates may be performed in one or more embodiments under vacuum with a pressure at or below 5 torr. Cannabinoid distillates may be obtained at a temperature of between 157 C and 230 C. In one or more embodiments, distillation may also yield terpene distillates, for example at a temperature between 140 C and 157 C. Distillation of these products may be performed multiple times to increase concentration or purity, followed by blending of terpene oil with the cannabinoid distillates.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A system and method for producing a terpene-enhanced cannabinoid concentrate will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
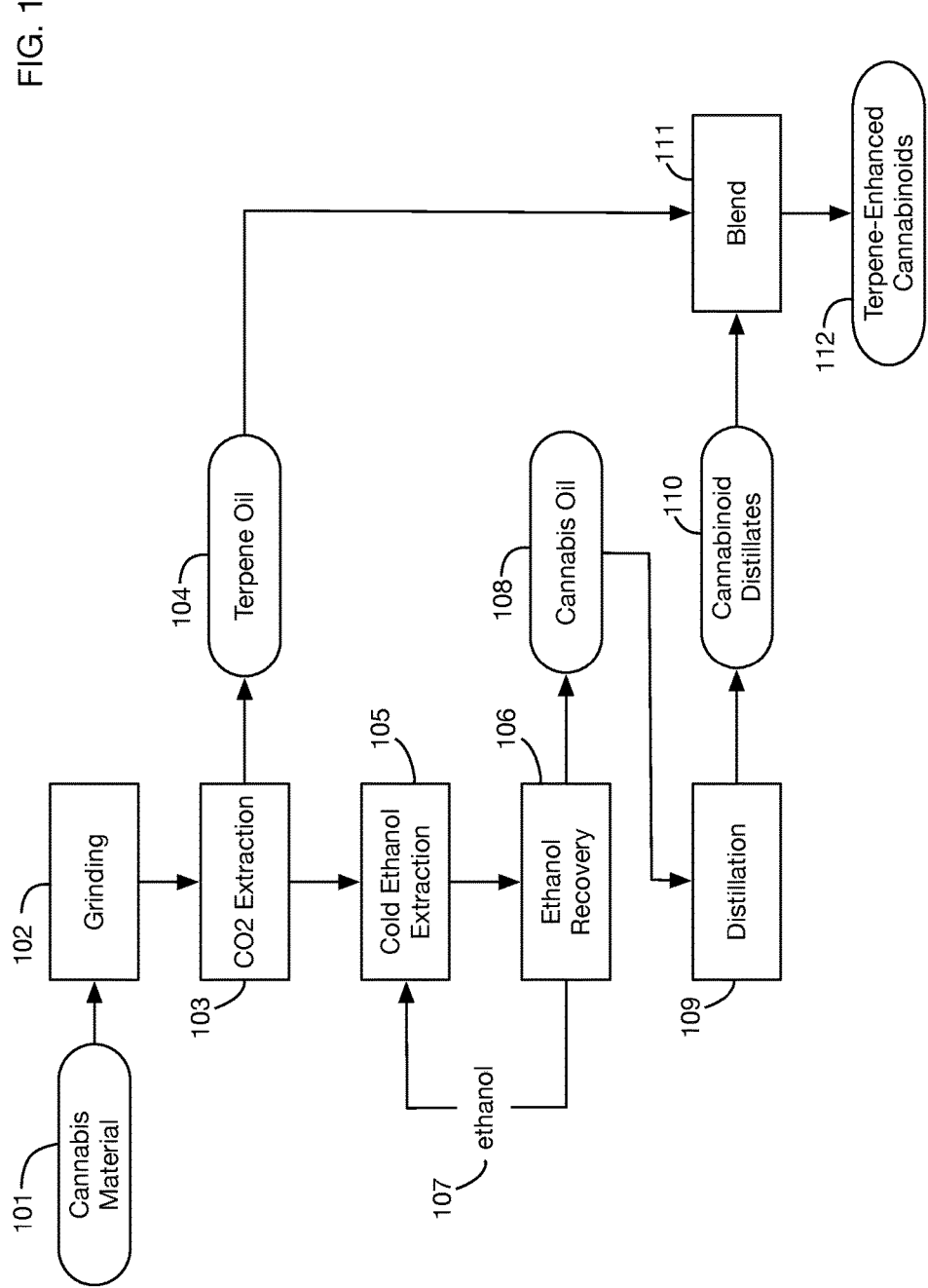
FIG. 1 shows a high-level flowchart of an embodiment of a method for producing a terpene-enhanced cannabinoid concentrate.

FIG. 1 shows a high-level flowchart of an embodiment of the invention. The steps shown are illustrative; one or more embodiments may use additional steps, or a subset of the steps shown. One or more embodiments may perform these steps in any desired order. One or more embodiments may perform one or more of these steps in parallel. The process shown in FIG. 1 generates a cannabinoid extract 112 that is enhanced with terpenes. Addition of terpenes to the cannabinoid extract may add flavor and may introduce compounds into the final blend that may have beneficial effects. The process may be performed at any scale, ranging for example from a micro scale such as on a benchtop to a large industrial scale such as in a refinery.

In the illustrative flowchart of FIG. 1, raw *cannabis* material 101 is obtained and is input into the grinding step 102. *Cannabis* material 101 may include for example, without limitation, the leaves, flowers, or buds of one or more *cannabis* plants. The flowers or buds have the highest concentration of cannabinoids and terpenes; however, any part or parts of the *cannabis* plant may be processed. The grinding step 102 may use any grinding method or methods, such as hand grinding, machine grinding, or use of a chipper or mulcher. In one or more embodiments, the grinding step may grind the material to a particle size similar to that of typical coffee grounds. Initial grinding may be followed in one or more embodiments by one or more filtering stages, for example to filter out stems or sticks. An illustrative mesh size used in one or more embodiments for filtering may be in the range of ¼ inch to ½ inch.

Grinding step 102 may be followed by CO2 extraction step 103. This step may be used for example to extract a terpene oil 104 from the ground plant material; some or all of this oil may be added back into the refined material in a later stage, as illustrated in blending step 111 in FIG. 1. CO2 extraction may for example extract terpenes more effectively and completely from *cannabis* material than the steam distillation process that is generally used for terpene extraction. CO2 extraction 103 may for example use a supercritical CO2 fluid. In this process CO2 is pressurized to form a liquid, and the liquid is mixed with the ground *cannabis* material to extract the desired compounds (in this case, terpenes). The CO2 may be removed from the solution by reducing the pressure, which allows the CO2 to evaporate as a gas and leaves the terpene extract behind. Illustrative process parameters used in one or more embodiments for the CO2 extraction step include: CO2 pressure in the range of 1000 psi to 1300 psi for the extraction; extraction temperature in the range of 80 F to 110 F; and separation temperature (after extraction) in the range of 40 F to 70 F. Run time for the CO2 extraction step may be for example in the range of 15 minutes to 6 hours.

After the extraction into the CO2 solution, terpene oils and hydrosols may be harvested from the solution. The oil may contain for example a mixture of terpenes and some cannabinoids, and the hydrosol may contain water-based terpenes and water. After removing the CO2 (via evaporation, for example), the remaining solution may be separated by allowing it to settle until the oil and the hydrosols separate, and then bleeding off the hydrosols. These products may then be filtered to remove waxes and cannabinoids by chilling them to a temperature in the range −80 F to 40 F, and then filtering with a coffee filter or a lower micron filter, for example with a pore size above 0.25 microns. Terpene oil 104 extracted in step 103 may be useful as a separate product (such as an essential oil), or it may be blended into further cannabinoid extracts in blending step 111.

Terpenes present in the extracted terpene oil and terpene hydrosol may include for example, without limitation, any or all of the terpenes alpha-Bisabolol, Camphene, 3-Carene, beta-Caryophyllene, Citronellol, Cymene, Eucalyptol, Famesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene. Hydrosols may include primarily humelene and pinene, but any other terpenes may also be present in the hydrosols. Typical terpene concentration in hydrosols may be in the range of 1% to 10%, while typical terpene concentration in terpene oil may be up to 99%. Hydrosols and oil may also include some cannabinoids, for example up to 15% cannabinoids in terpene oils and up to 5% in hydrosols. The terpene oil and terpene hydrosols may be used for example as flavoring, or in aroma therapy products, in salves, in creams, or in topical treatments. These terpene compounds may have medicinal uses when taken internally or applied externally.

After extracting terpenes in step 103, the remaining non-extracted plant material may then be processed in cold ethanol extraction step 105. For example, the plant material that was exposed to the CO2 may be emptied from the CO2 extraction vessel and placed into one or more sanitary steel tubes, which may then be placed into a cryogenic freezer or other cooling apparatus to cool the plant material to a temperature in the range of −80 F to 30 F. Each tube may then be attached to a catch pot, possibly with a filter between the tube and the catch pot, and cold ethanol may be introduced into the tube and exposed to the plant material. After exposure, a dump valve may be opened to allow the cold ethanol solution to flow into the catch pot. A vacuum may also be applied to facilitate removal of the cold ethanol solution from the tube. The tube may be flushed for example for a time in the range of 5 minutes to 30 minutes. Flushing may continue for example until the ethanol stops or until it begins to turn greenish in color. The catch pot then contains an ethanol oil solution with extracted compounds from the plant material.

The ethanol oil solution may then be processed in ethanol recovery step 106 to remove some or all of the ethanol from the solution, leaving a *cannabis* oil product 108. As illustrated in FIG. 1, some or all of the recovered ethanol 107 may be recycled into the cold ethanol extraction step 105. The ethanol recovery process may for example use a vacuum distillation method to remove ethanol from the solution. The ethanol oil solution may be transferred into a recovery column which may be warmed in a water bath or in a jacketed column, for example to a temperature in the range of 120 F to 165 F. The recovery column may be connected to a condenser with circulating cold water and connected to a vacuum to accelerate ethanol evaporation. In an illustrative ethanol recovery process, after starting the cold water circulation the vacuum pump level may be set in the range of −10 inches Hg to −25 inches Hg. Condensed ethanol may be recovered into a container, which may then be used as input to the cold ethanol wash step for subsequent batches. Recovery run time may for example range from approximately 30 minutes to 3 hours, yielding recovered ethanol at a rate of approximately 7.5 L to 10 L per hour.

The remaining oil in the recovery column after the ethanol recovery step is an organic cannabinoid concentrated oil 108. This oil may be referred to colloquially (although not completely correctly) as "Rick Simpson Oil," or "RSO." It may contain for example cannabinoids in a concentration of approximately 50% to 90%, and may contain for example up to 20% terpenes. Cannabinoids contained in the oil may include for example, without limitation, THCa, THC, THCV, CBDa, CBD, CBC, CBG, and CBN. The oil may be processed further to form a concentrate (as described below), or it may be used directly as a final product. The oil may be smoked or vaped, for example as a "shatter" or in a vape pen as an oil. It may be activated, for example by heating in an oven to approximately 180 F, and incorporated into edible products, topicals, creams, or salves.

The *cannabis* oil 108 may then be further concentrated in distillation step 109. Distillation 109 may for example use any distillation devices and techniques, including for example, without limitation, short path distillation, thin film distillation, wipe film distillation, and spinning band distillation. An illustrative distillation process is as follows. The *cannabis* oil 108 is placed on a hot plate with a stir rod or stir bar, at a temperature of no more than 140 C in one or more embodiments. Distillation may be performed under vacuum or without vacuum. With a vacuum under 5 torr, most terpenes distill out before 157 C; cannabinoid distillates 110 distill out between 157 C and 185 C; and some additional products such as CBG, CBN, and THCV distill out between 185 C and 230 C. Without a vacuum, distillation may be performed for example between 370 C and 440 C. In one or more embodiments, the products of distillation may be redistilled, possibly multiple times, to increase the concentration of the final product. The cannabinoid distillates 110 may for example have cannabinoid concentrations between 80% and 99.99%, with higher levels possible using multiple distillations. Cannabinoid distillates may be smoked or vaped, for example as a "shatter" or in a vape pen as an oil. They are already activated as a result of the distillation process; therefore, they may be incorporated into edible products, topicals, creams, or salves.

In one or more embodiments, the cannabinoid distillates 110 may be blended in step 111 with the terpene oil 104 extracted using CO2 extraction 103, to create a terpene-enhanced cannabinoid concentrate 112. This blending may for example add flavor and may create additional effects when smoking, vaping, or ingesting the blend. Blending terpene oil with the cannabinoid distillates may also make the product 112 thin enough to be used in vape pens. In one or more embodiments, the blending step 111 may use a ratio by volume of terpene oil to cannabinoid distillates in the range 1:25 to 1:5. An illustrative embodiment may use for example a ratio of terpene oil to cannabinoid distillates of 1:10.

Figure 2:
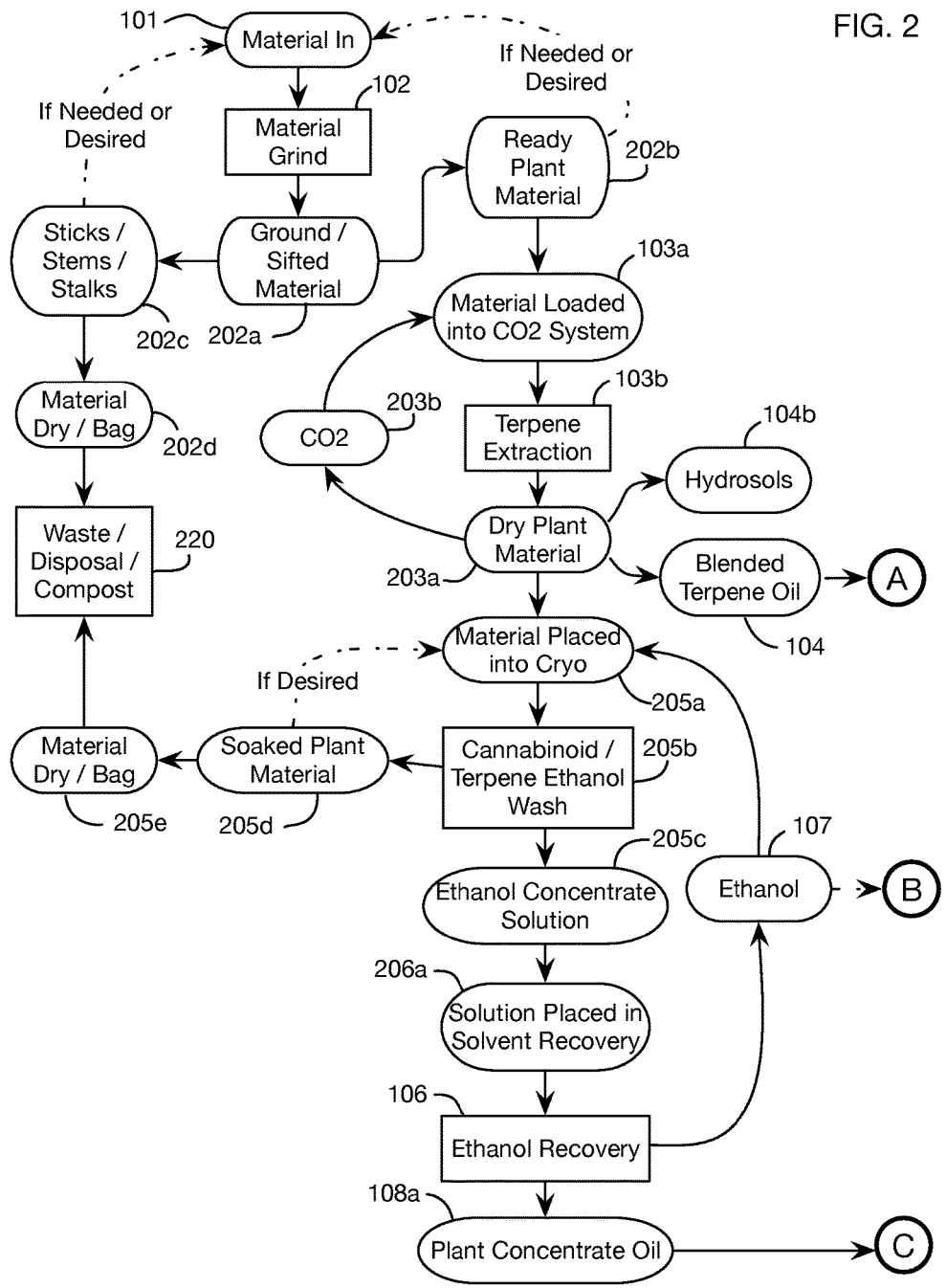
FIGS. 2 and 3 show a detailed flowchart of an embodiment of the invention, illustrating steps, products, and optional flow paths in the process.
Figure 3:
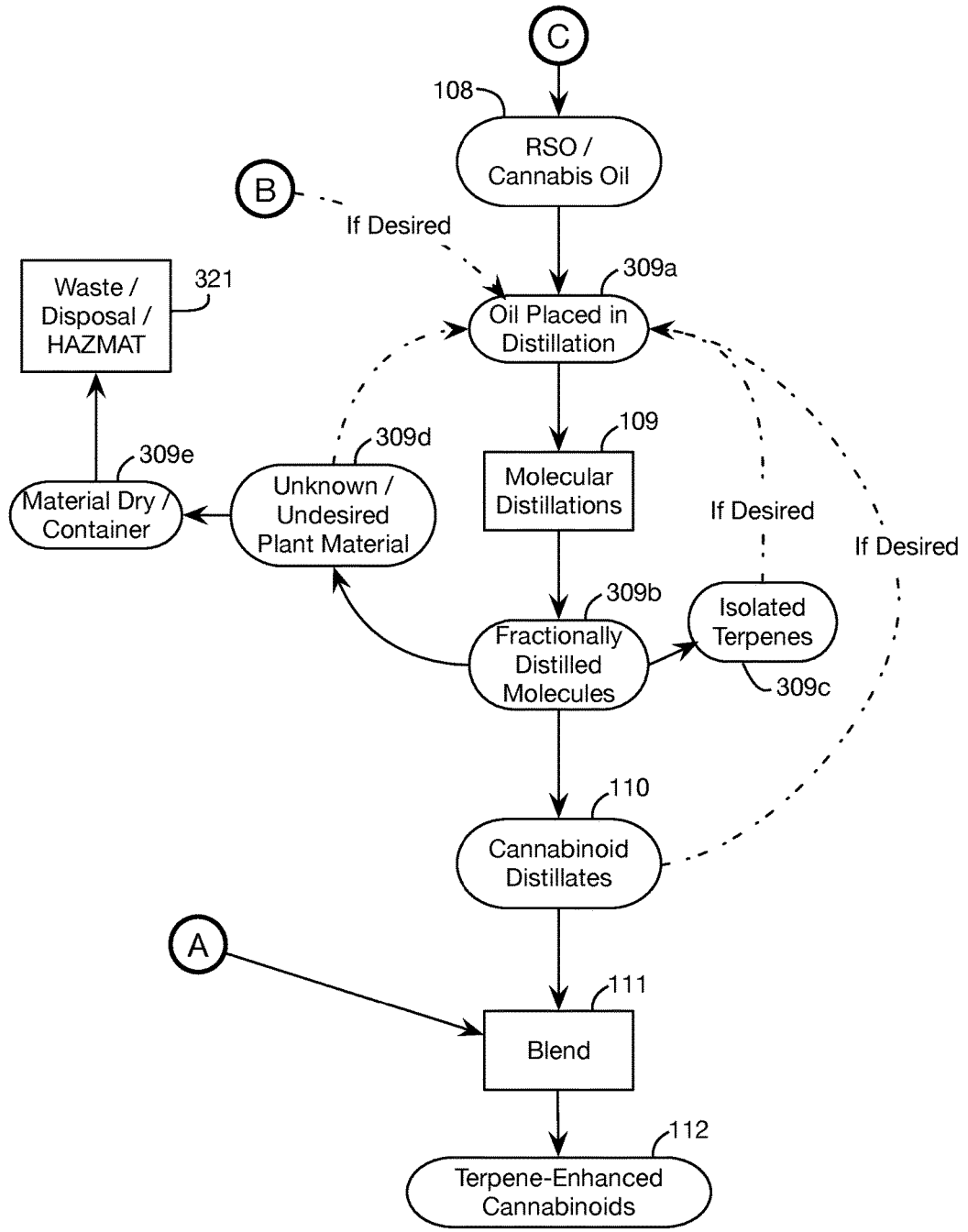

FIGS. 2 and 3 show a more detailed flowchart of an embodiment of the invention. (FIG. 3 is a continuation of FIG. 2). *Cannabis* material 101 is input into grinding step 102, yielding ground/sifted material 202a. This material 202a is then filtered to remove sticks, stems, and stalks 202c. The remaining ready plant material 202b is input into the CO2 extraction process. If needed or desired, additional grinding, sifting, and filtering may be performed on either or both of the sticks, stems, and stalks 202c, and the ready plant material 202b, prior to CO2 extraction. Unused stems, sticks and stalks 202c are dried and bagged into waste products 202c, and sent to a waste disposal/composting process 220.

The material 202b is then loaded into a CO2 extraction vessel, forming loaded material 103a. Terpene extraction 103b is then performed using CO2 203b as a solvent. This extraction yields terpene oil 104 and terpene hydrosols 104b. The remaining dry plant material 203a is further processed with the next steps in the process. CO2 203b removed from the solution may be recycled and used for additional terpene extraction steps 103b.

The cold ethanol extraction process then proceeds with dry plant material 203a placed into a container and cryogenically frozen, yielding frozen material 205a. Ethanol wash 205b is then performed over this frozen material, yielding ethanol concentrate solution 205c. The remaining soaked plant material 205d may be reprocessed with additional cryogenic freezing 205a and ethanol wash 205b if desired, or formed into waste material 205e that is transmitted to waste disposal/composting process 220. The solution 205c is then transferred to a solvent recovery vessel 206a, and ethanol recovery process 106 removes ethanol 107 from the solution. The ethanol may be recycled if desired for subsequent cold ethanol extraction steps. After removing ethanol, the solution contains plant concentrate oil 108a.

Turning now to FIG. 3, which is a continuation of FIG. 2, plant concentrate oil 108a ("C" from FIG. 2) may be used directly as *cannabis* oil 108 (also referred to colloquially as "RSO"). It may also be further processed with distillation and blending. Oil 108 may be placed in a distillation vessel 309a. In addition, if desired, some or all of the ethanol 107 removed from the oil ("B" from FIG. 2) may be further distilled to obtain any residual cannabinoids or other products. Molecular distillation steps 109 may yield various fractionally distilled products 309b (for example at different distillation temperatures), including cannabinoid distillates 110 and isolated terpenes 309a. Remaining plant material 309d after distillation to extract products 110 and 309c may be transformed into waste 309e and disposed in step 321, or it may be redistilled. Products 110 and 309c may also be redistilled, for example to increase product concentration. Cannabinoid distillates 110 may then be blended with the terpene oil 104 from CO extraction ("A" from FIG. 1), yielding terpene-enhanced cannabinoid oil 112.

Figure 4:
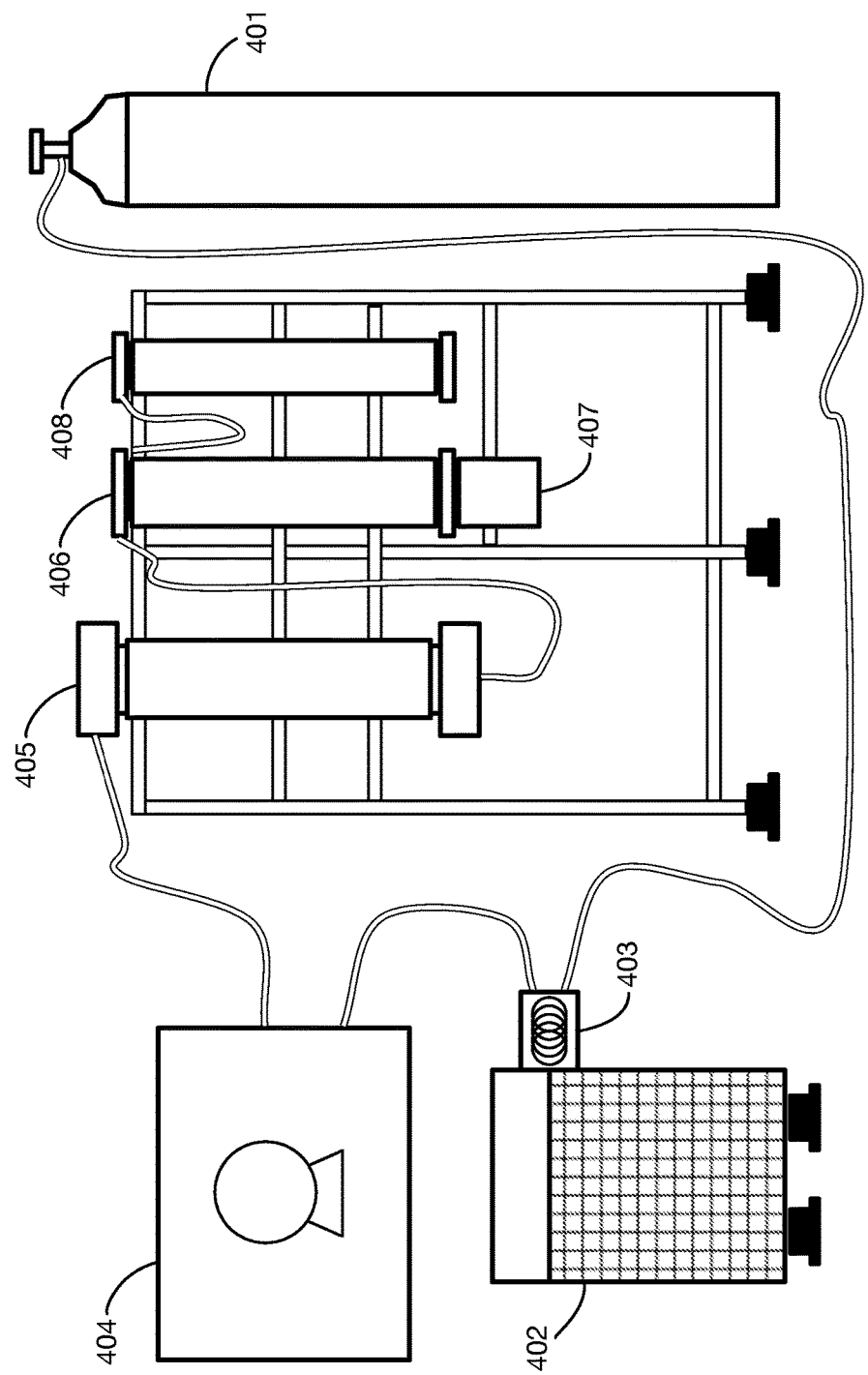
FIG. 4 shows illustrative equipment that may be used in the CO2 extraction step of the process of FIG. 1.

FIGS. 4 through 9 show illustrative equipment that may be used in one or more steps of the process in one or more embodiments of the invention. This equipment is illustrative; one or more embodiments may use any desired equipment for any step or steps. Any of the steps may be manual, automated, or semi-automated. FIG. 4 shows illustrative equipment that may be used for CO2 extraction in one or more embodiments of the invention. CO2 extraction may for example use an Apeks® 1500-20L Botanical Oil Extraction System, or any similar equipment. FIG. 4 shows selected components of the system; it does not show all components and all connections. CO2 gas is obtained from CO2 tank 401. This gas flows to chiller 402, which cools the gas using heat exchanger 403. The pressure of the gas is increased with compression pump 404, yielding a supercritical CO2 fluid. This fluid is passed over ground and frozen *cannabis* material in extraction vessel 405. The CO2 solution with extracted terpenes then flows to separation vessel 406, which has a collection cup 407 at the bottom. The CO2 evaporates from vessel 406, leaving the terpene oil and hydrosols in collection cup 407. If desired or needed, further separation may be performed using separation vessel 408.

Figure 5:
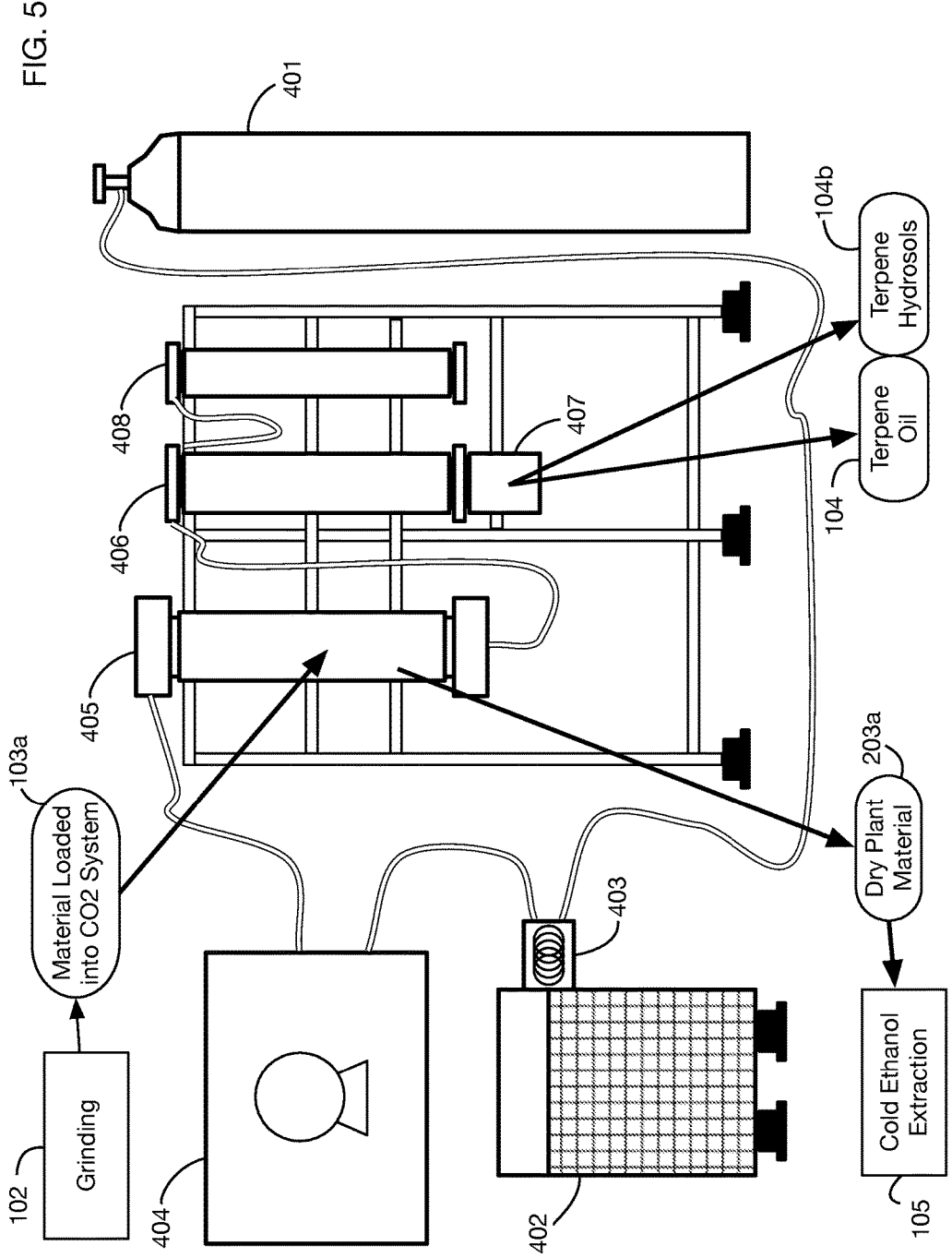
FIG. 5 shows how the equipment of FIG. 4 relates to selected steps and products shown in the process flowchart of FIGS. 2 and 3.

FIG. 5 annotates the equipment of FIG. 4 with selected process steps and products from the flowchart of FIGS. 2 and 3. After grinding 102, material 103a is loaded into the CO2 system in extraction vessel 405. The products of CO2 extraction including terpene oil 104 and terpene hydrosols 104b are collected in collection cub 407. After CO2 extraction, the plant material 203a remaining in vessel 405 is removed and is transferred to cold ethanol extraction step 105, which is described next.

Figure 6:
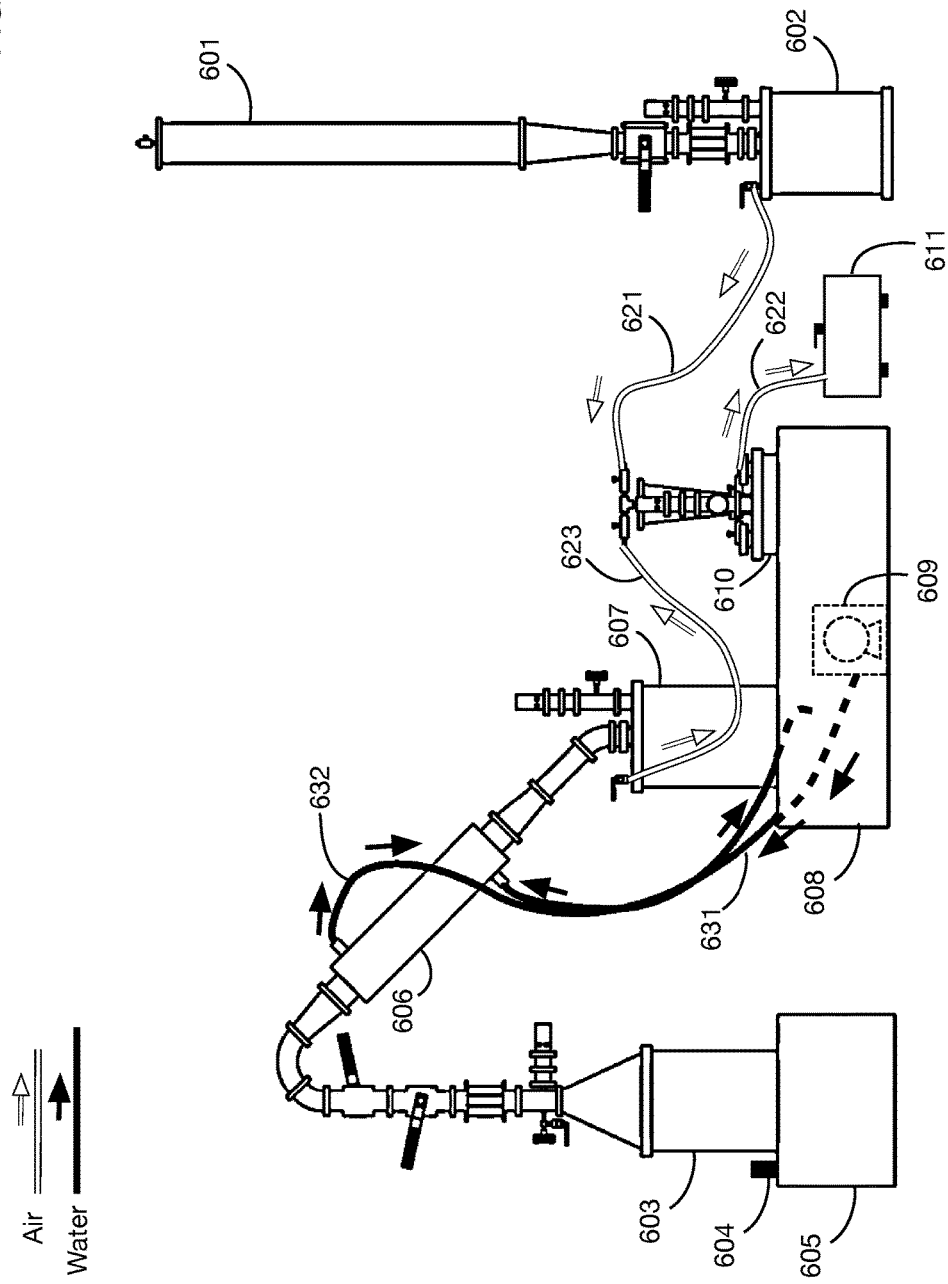
FIG. 6 shows illustrative equipment that may be used in the cold ethanol extraction and ethanol recovery steps of the process of FIG. 1.

FIG. 6 shows illustrative equipment that may be used for cold ethanol extraction in one or more embodiments of the invention. Frozen plant material is placed into tube 601, which is flushed with cold ethanol. The cold ethanol solution containing extracted compounds is drained into receiving vessel 602, assisted by a vacuum. The vacuum pump 611 pulls air through line 621 to a connection at the top of vacuum cold trap 610, and from the cold trap through line 622 to the pump. The ethanol solution is then transferred to container 603, which is placed into hot water bath 605. The hot water bath is heated by heating element 604. The heat causes the ethanol in the solution to evaporate; ethanol vapor reaches condenser 606 which is cooled by cold water flowing from cold solution bath 608 through water line 631, and then returned via line 632 to the cold bath 608. Water flow is driven by pump 609 in the cold solution bath. Distillation of ethanol is vacuum assisted with vacuum line 623 attached to receiving vessel 607 that collects condensed ethanol. An additional vacuum cold trap 610 captures residual ethanol that may be in the vacuum line.

Figure 7:
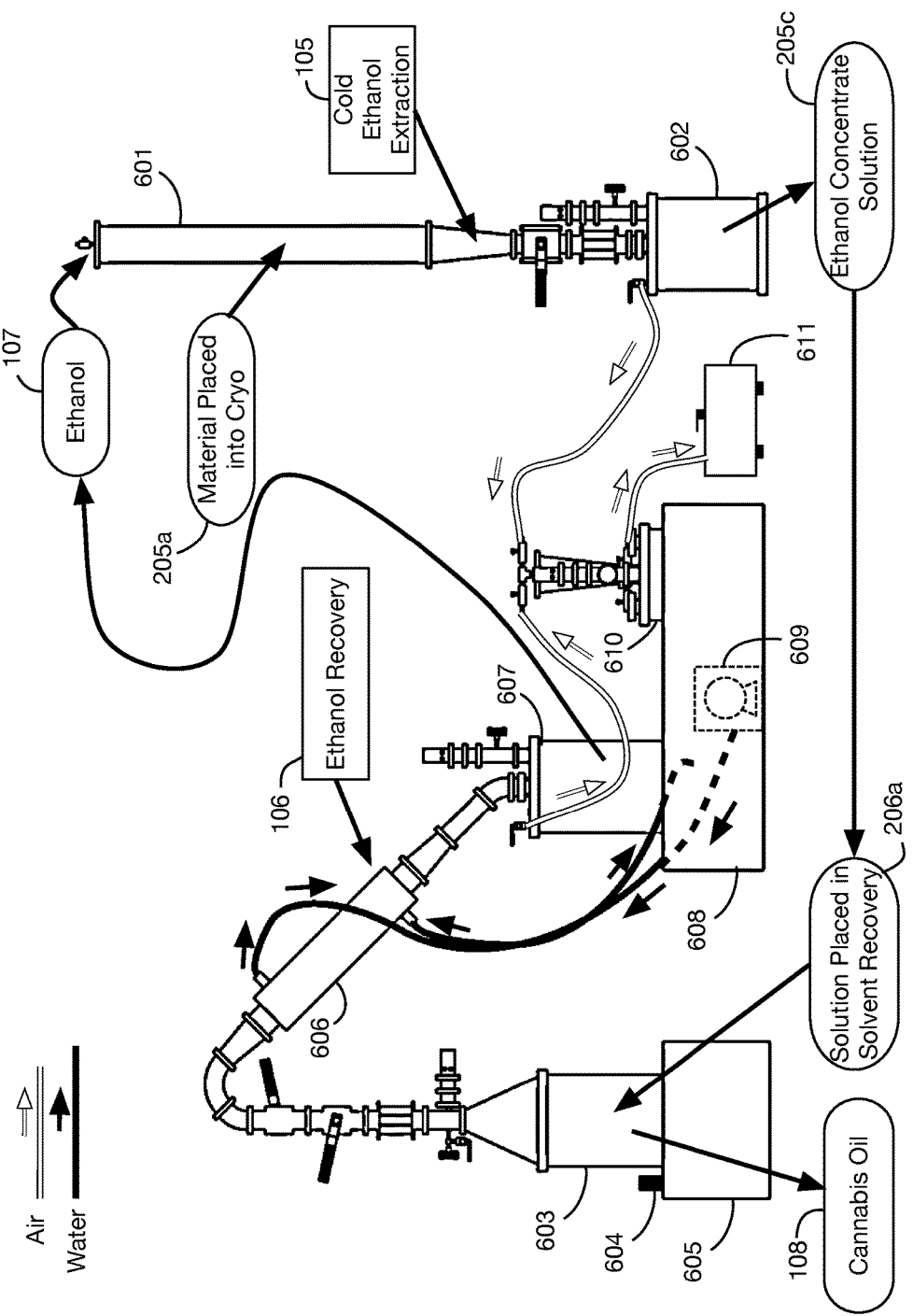
FIG. 7 shows how the equipment of FIG. 6 relates to selected steps and products shown in the process flowchart of FIGS. 2 and 3.

FIG. 7 annotates the equipment of FIG. 6 with selected process steps and products from the flowchart of FIGS. 2 and 3. Material 205a that is cryogenically frozen is placed into tube 601. Ethanol 107 is added to the tube and cold ethanol extraction step 105 removes the ethanol concentrate solution 205c from tube 601 into receiving container 602. This solution 205c is then transferred to container 603 as solution 206a for solvent (ethanol) recovery. Ethanol recovery step 106 occurs in condenser 606 (and possibly in vacuum cold trap 610 as well) as ethanol vapor condenses, and recovered ethanol is collected in container 607 (and possibly in container 610). This recovered ethanol 107 may be recycled for additional cold ethanol flushes of material in tube 601. The material remaining in container 603 after ethanol recovery is *cannabis* oil 108.

Figure 8:
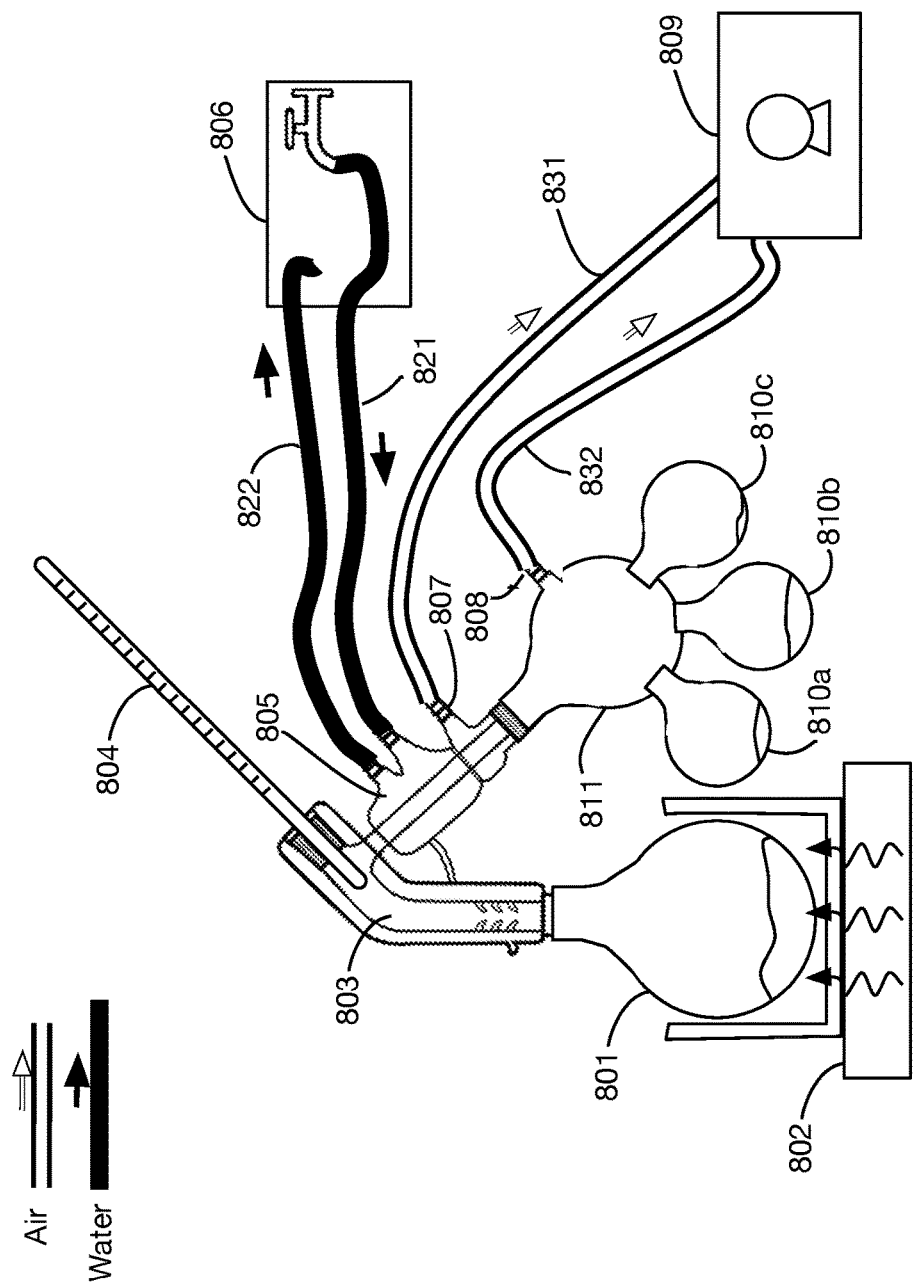
FIG. 8 shows illustrative equipment that may be used in the distillation step of the process of FIG. 1.

FIG. 8 shows illustrative equipment that may be used for *cannabis* oil distillation in one or more embodiments of the invention. This figure shows a short path distillation process; one or more embodiments may use any desired distillation process, including but not limited to short path distillation. Flask 801 containing *cannabis* oil is placed on heating element 802. Distillation head 803 attached to flask 801 has an attached thermometer 804, and has connections for vacuum and water. Water line 821 provides cooling water to the condenser water jacket 805 from water source 806, and return water line 822 drains or recirculates this water. Vacuum line 831 attaches connection 807 to vacuum pump 809, and vacuum line 832 attaches to connection 808 on distribution bulb 811. In this illustrative embodiment, three collection flasks 810a, 810b, and 810c are attached to distribution bulb 811.

Figure 9:
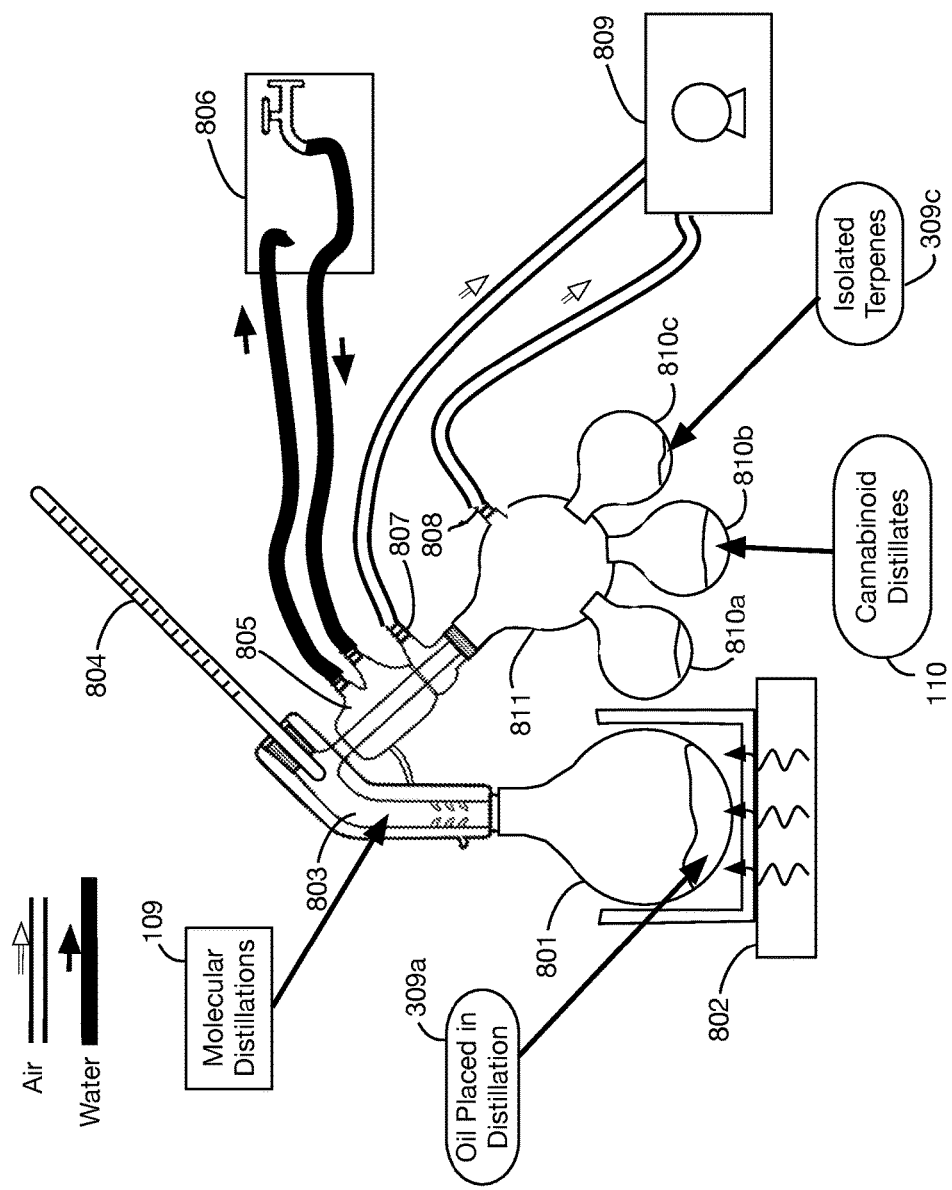
FIG. 9 shows how the equipment of FIG. 8 relates to selected steps and products shown in the process flowchart of FIGS. 2 and 3.

FIG. 9 annotates the equipment of FIG. 8 with selected process steps and products from the flowchart of FIGS. 2 and 3. *Cannabis* oil placed in distillation 309a is placed in flask 801. Molecular distillations 109 occur in distribution head 803, and distillation products such as cannabinoid distillates 110 and isolated terpenes 309c are collected in collection flasks 810a, 810b, or 810c. Thermometer 804 may be used to monitor the distillation temperature in order to separate and identify products such as cannabinoid distillates 110 and terpene distillates 309c that distill out at different temperatures.

While the invention herein disclosed has been described by means of specific embodiments and applications thereof, numerous modifications and variations could be made thereto by those skilled in the art without departing from the scope of the invention set forth in the claims.

What is claimed is:

1. A method for producing a terpene oil enhanced cannabinoid concentrate comprising:
   obtaining *cannabis;*
   grinding said *cannabis* to obtain a ground *cannabis;*
   extracting terpene hydrosol terpene oil from said ground *cannabis* using carbon dioxide to yield a residual ground *cannabis* and said terpene oil;
   separating said terpene oil from said residual ground *cannabis;*
   freezing said residual ground *cannabis* to obtain a frozen residual *cannabis;*
   washing said frozen residual *cannabis* with cold ethanol to obtain an ethanol oil solution of *cannabis;*
   separating said ethanol oil solution of *cannabis* into ethanol and *cannabis* oil separately;
   distilling said *cannabis* oil to obtain cannabinoid distillates; and,
   blending said cannabinoid distillates with said terpene oil to obtain said terpene oil enhanced cannabinoid concentrate, wherein said terpene oil is extracted from said ground *cannabis* by:
   pressurizing said carbon dioxide to a pressure between 1000 psi and 1300 psi to form a supercritical carbon dioxide fluid;
   exposing said ground *cannabis* to said supercritical carbon dioxide fluid at a temperature between 80° F. and 110° F. for an elapsed time between 15 minutes and 6 hours to obtain a carbon dioxide extraction solution;

reducing the pressure of said carbon dioxide extraction solution to remove said carbon dioxide, thereby obtaining a carbon dioxide extraction product;

separating said carbon dioxide extraction product into said terpene oil; and, filtering said terpene oil at a temperature between −80° F. and 40° F. with a filter having a pore size greater than 0.25 micron.

2. The method of claim 1 wherein said cannabinoid distillates comprise Tetrahydrocannabinol and Cannabidiol.

3. The method of claim 2 wherein said cannabinoid distillates further comprise one or more of Cannabigerol, Cannabinol, and Tetrahydrocannabivarin.

4. The method of claim 1 wherein a concentration of cannabinoids in said cannabinoid distillates is at least 80%.

5. The method of claim 1 wherein said terpene oil comprises one or more of alpha-Bisabolol, Camphene, 3-Carene, beta-Caryophyllene, Citronellol, Cymene, Eucalyptol, Farnesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene.

6. The method of claim 1 wherein said cold ethanol has a temperature of 30° F. or below.

7. The method of claim 1 wherein said separating said ethanol oil solution of *cannabis* into ethanol and *cannabis* oil separately comprises distilling said ethanol oil solution of *cannabis* at a temperature between 120° F. and 165° F. under a vacuum measuring between 10 inches Hg and 25 inches Hg.

8. The method of claim 7 further comprising reusing said ethanol for a subsequent washing step of a second batch of frozen residual *cannabis*.

9. The method of claim 1 wherein said distilling comprises generating a vacuum in a distillation vessel with a pressure at or below 5 torr;

heating said *cannabis* oil to a temperature between 157° C. and 230° C.; and, collecting a condensed vapor to yield said cannabinoid distillates.

10. The method of claim 9 wherein said distilling further comprises heating said *cannabis* oil to a temperature between 140° C. and 157° C.; and, collecting a first condensed vapor to yield terpene distillates.

11. The method of claim 1 further comprising redistilling said cannabinoid distillates to obtain a higher concentration of cannabinoid distillates; and blending said higher concentration of cannabinoid distillates with said terpene oil to obtain a higher concentration of said terpene oil enhanced cannabinoid concentrate.

12. The method of claim 1 wherein a ratio by volume of said terpene oil to said cannabinoid distillates in said terpene oil enhanced cannabinoid concentrate is in a range of 1:25 to 1:5.

13. The method of claim 1 wherein a ratio by volume of said terpene oil to said cannabinoid distillates in said terpene oil enhanced cannabinoid concentrate is in a range of 1:12 to 1:8.

14. The method of claim 1 wherein a ratio by volume of said terpene oil to said cannabinoid distillates in said terpene oil enhanced cannabinoid concentrate is 1:10.

15. The method of claim 1, wherein said extracting terpene oil further comprises separating a terpene hydrosol from said carbon dioxide extraction product.

16. The method of claim 15, wherein said extracting terpene oil further comprises filtering said terpene hydrosol at a temperature between −80° F. and 40° F. with a filter having a pore size greater than 0.25 micron.

* * * * *